US006927051B1

(12) United States Patent
Wang

(10) Patent No.: US 6,927,051 B1
(45) Date of Patent: Aug. 9, 2005

(54) POLYMER-PROTEIN SURFACTANTS

(75) Inventor: Ping Wang, Fairlawn, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 10/116,611

(22) Filed: Apr. 4, 2002

(51) Int. Cl.$^7$ .......................... C12N 9/96; C12N 11/12; C11D 9/08; C11D 9/40; C11D 3/37
(52) U.S. Cl. ...................... 435/188; 435/179; 510/235; 510/421; 510/427; 510/492; 510/503; 510/510
(58) Field of Search .............................. 510/235, 427, 510/492, 503, 510, 421; 435/179, 188

(56) References Cited

U.S. PATENT DOCUMENTS

| | | | | |
|---|---|---|---|---|
| 3,925,157 A | | 12/1975 | Hamsher ....................... | 195/63 |
| 3,970,521 A | * | 7/1976 | Zaborsky et al. ............. | 435/179 |
| 3,985,616 A | | 10/1976 | Weaver et al. ................ | 195/63 |
| 3,985,617 A | | 10/1976 | Yugari et al. ................. | 195/68 |
| 4,008,126 A | | 2/1977 | Keyes ........................... | 195/63 |
| 4,141,857 A | | 2/1979 | Levy et al. ................... | 252/430 |
| 4,371,612 A | | 2/1983 | Matsumoto et al. .......... | 435/44 |
| 4,539,294 A | | 9/1985 | Metcalfe et al. ............. | 435/180 |
| 4,727,030 A | | 2/1988 | Ishimura et al. ............. | 435/182 |
| 4,978,619 A | | 12/1990 | Kajiwara et al. ............ | 435/182 |
| 5,441,660 A | | 8/1995 | Tsaur et al. ................... | 252/95 |
| 5,482,996 A | | 1/1996 | Russell et al. ............... | 525/54.1 |
| 5,719,039 A | | 2/1998 | Dordick et al. ............... | 435/41 |
| 5,770,559 A | * | 6/1998 | Manning et al. .............. | 514/2 |
| 5,882,520 A | | 3/1999 | Richards et al. ............. | 210/632 |
| 5,914,367 A | | 6/1999 | Dordick et al. ............... | 525/54.1 |
| 6,613,358 B2 | * | 9/2003 | Randolph et al. ............ | 424/489 |

OTHER PUBLICATIONS

"Biocatalytic Plastics as Active and Stable Materials for Biotransformations" by Wang et al., *Nature Biotechnology*, 15, pp. 789-793, 1997.
"Activity and Stability of Enzymes Incorporation into Acyclic Polymers" by Yang et al., *J. Amer. Chem. Soc.*, 117, pp. 4843-4350, 1995.
"Immobilization of β-Galactosidase onto Polymeric Supports" by Rejikumar et al., *J. Appl. Poly. Sci.*, 55, pp. 871-878, 1995.
"Hydrophilic Urethane Propolymers: Convenient Materials for Enzyme Entrapment" by Fukushima et al., *Biotech. Bioeng.*, 20, pp. 1465-1469, 1978.
"Cross-linked Polyacrylamide Derivatives as Water-Insoluble Carriers of Amylolytic Enzymes" by Barker et al., *Carbohydrate Research*, 14, pp. 287-296, 1970.

\* cited by examiner

*Primary Examiner*—Jon Weber
*Assistant Examiner*—Kailash C. Srivastava
(74) *Attorney, Agent, or Firm*—Roetzel & Andress LLC

(57) ABSTRACT

An enzymatic chemical process comprising the steps of providing a biphasic liquid medium that includes one polar phase and one nonpolar phase in contact with each other, wherein at least one of the phases includes reactants, and adding a polymer-protein surfactant to the biphasic liquid medium, whereby the polymer-protein surfactant will self-assemble at the interface between the polar and nonpolar phases and catalyze reactions involving the reactants.

2 Claims, No Drawings

POLYMER-PROTEIN SURFACTANTS

FIELD OF THE INVENTION

This invention relates to polymer-modified proteins and their use as enzymatic catalysts at a biphasic polar-nonpolar liquid interface.

BACKGROUND OF THE INVENTION

Traditional chemical processes can be harmful to the environment. Enzymatic bioprocessing, on the other hand, uses enzymes to catalyze chemical reactions, and therefore, represents an important approach in developing environmentally safe processes for applications such as bulk chemical production and drug synthesis. Enzymatic bioprocessing can be used in producing chemical intermediates such as alkene epoxides and glycosides; the former are among the top 50 commodity chemicals in the United States and the latter are commonly used in drug synthesis. Additional enzymatic bioprocessing applications include oxidizing organic pollutants such as polycyclic aromatic hydrocarbons and enzymatically desulfurizing and refining petroleum.

Unfortunately, the prior art has failed to yield an efficient means for performing enzymatic bioprocessing partly because of an enzyme's inherent hydrophilicity. Many significant enzymatically-catalyzed reactions involve both hydrophilic and hydrophobic reactants dissolved in polar and nonpolar solvents respectively. The unmodified catalytic enzymes, which hereinafter may be referred to as native enzymes, have a hydrophilic nature that only allows them to effectively dissolve in polar solvents, e.g., water. Therefore, their very nature limits their accessibility to reactants in a nonpolar solvent.

When hydrophilic and hydrophobic reactants are dissolved in separate immiscible solvents, enzymatic catalysis and chemical reaction can only occur at the interface created where the polar and nonpolar liquids are in contact. But the bulk of the reactants and enzymes in solution rarely reach the biphasic interface due to their individual kinetics, and when they do, it is only momentary. With respect to all of the native enzymes in solution, only a very small number are available at the biphasic interface at any point in time. The unavailability of reactants and enzymatic catalysts at the interface, i.e., reaction site, significantly contributes to the bioprocess's overall inefficiency. Thus, the reaction rates of these traditional enzymatic bioprocesses are slow in comparison to those of traditional chemical processes.

There are exceptions to the general rule regarding an enzyme's hydrophilicity. Certain proteins can bind to lipid membranes via Coulombic force, Born repulsion, and hydrophobic interactions; with electrostatic interactions between the positively charged protein domain and the negatively charged lipid membrane being considered the key driving force in most cases. Lipases, which hydrolyze triacylglycerol lipids, are a unique class of enzymes that assemble at a lipid-water interface through hydrophobic interactions. It has been revealed that pancreatic lipase assembles at a lipid-water interface via complexation with pancreatic colipase, which provides the necessary hydrophobicity. Other lipases such as *Rhizomucor miehei* lipase have surfaces with sufficient hydrophobicity to enable assembling at a lipid-water interface. Enzymes other than lipases generally lack the hydrophobicity for assembly at organic-aqueous interfaces.

Attempts have been made to manipulate the hydrophilic nature of enzymes in order to make them more useful in nonpolar mediums. For example, V. M. Paradar and J. S. Dordick (*J. Am. Chem. Soc.,* 1994, vol. 116, 5009) demonstrated that enzymes can be ion-paired with surfactants and thereby form enzyme-surfactant ion-paired complexes; they can be formed by contacting an aqueous enzymatic solution with a nonpolar solution comprising surfactants such as AOT. Upon contact, electrostatic interactions cause the surfactants to pair with the enzymes, and the resulting enzyme-surfactant complex is soluble in nonpolar solvents. These complexes have been found particularly useful as enzymatic catalysts in reactions occurring in nonpolar solvents. However, the complexes are not useful in biphasic polar-nonpolar liquid reaction systems.

Similarly, other attempts to manipulate the lipophobicity of enzymes also include chemical modification, such as attaching polyethylene glycol (PEG) (for example, see C. Pina, D. Clark, H. Blanche and I. G. Gonegani, *Biotechnology Techniques,* 2989, vol. 3, 333; P. Wang, C. A. Woodward, E. N. Kaufman, *Biotechno. Bioeng.,* 1999, vol. 64, 290; Z. Yang, *Progress in Biochemistry and Biophysics,* 1995, vol. 22, 340). Examples of further attempts include deglycosylation followed by attaching benzyl groups (see R. Vazquez-Duhalt, P. M. Fedorak, *Enz. Micro. Tech.* 1992, vol. 14, 837). Again, these manipulations all result in modified enzymes that are suitable for use in monophasic systems such as polar or nonpolar solvents, but not the immiscible biphasic systems addressed with this invention.

SUMMARY OF THE INVENTION

In general the present invention provides an enzymatic chemical process comprising the steps of providing a biphasic liquid medium that includes one polar phase and one nonpolar phase in contact with each other, wherein at least one of the phases includes reactants, and adding a polymer-protein surfactant to the biphasic liquid medium, whereby the polymer-protein surfactant will self-assemble at the interface between the polar and nonpolar phases and catalyze reactions involving the reactants.

The present invention also includes a chemical process for synthesizing polymer-protein surfactants comprising the steps of providing a biphasic liquid medium that includes one polar phase and one nonpolar phase in contact with each other, and adding functionalized polymer to the nonpolar phase and protein to the polar phase.

The present invention further provides a polymer-protein surfactant comprising an enzymatic substituent and a polymeric substituent.

The present invention also includes a chemical process for synthesizing PPS comprising the steps of providing a biphasic medium that includes one solid phase and one polar liquid phase wherein the two phases are in contact with each other, and adding protein to the polar phase.

The interfacial biocatalyst of this invention increases the enzymatic catalytic efficiency of enzymes with respect to reactions occurring at a polar-nonpolar biphasic liquid interface. The enzymes are chemically modified by attaching a hydrophobic polymer chain thereto, which promotes localized concentrations of hydrophilic enzymes at a biphasic polar-nonpolar liquid interface. Modification results in enzyme-polymer conjugates having surfactant-like properties that promote self-assembly at the interface. And whose positioning at the interface therefore provides reagents and/or cofactors in the nonpolar medium with improved accessibility to the catalytic enzyme. Catalytic availability and overall reaction rates are improved as a result.

In addition, the hydrophobic polymer chain affects the microenvironmental interactions around the enzymes and thereby improves enzyme stability, i.e., extends enzyme catalytic lifetime at the interface and improves overall catalytic efficiency.

Native enzymes are generally unstable in the presence of nonpolar solvents and their effective catalytic lifetime is relatively short compared to that of a polymer-modified protein. But surprisingly, an enzyme's catalytic efficiency and lifetime in the presence of a nonpolar solvent are improved when a nonpolar-polymer substituent is chemically bonded thereto. Polymer-modified proteins catalyze reactions faster than native enzymes by more than two orders of magnitude, and their catalytic lifetimes are up to three-times longer than those of native enzymes.

DETAILED DESCRIPTION OF ILLUSTRATIVE EMBODIMENTS

A polymer-modified protein of this invention may hereinafter be referred to as polymer-protein surfactant (PPS). PPS are catalytic molecules that will self-orient at a biphasic polar-nonpolar liquid interface. PPS include a hydrophilic-protein substituent and at least one hydrophobic polymer substituent and optionally a coupling agent that can be employed as an inert link between the two substituents. Where a coupling agent is not employed, the hydrophilic-protein substituent is chemically bonded directly to the hydrophobic-polymer substituent.

A hydrophilic-protein substituent derives from a hydrophilic enzyme that has been chemically reacted with a hydrophobic polymer or inert coupling agent. Likewise, a hydrophobic-polymer substituent derives from a polymer that has been chemically reacted with a hydrophilic-protein substituent or inert coupling agent. A coupling agent, when employed, derives from a multi-functional compound, where one of the functionalities can react with an enzyme and a separate functionality can react with a functionalized polymer. Apart from reacting with an enzyme and functionalized polymer, the coupling agent is otherwise chemically inert.

When immersed into a polar-nonpolar biphasic liquid medium, the hydrophobic-polymer substituent self-orients into the nonpolar liquid while the hydrophilic-protein substituent self-orients into the polar liquid. Due to the PPS's respective affinities for polar and nonpolar liquids, it will maintain its position at the polar-nonpolar liquid interface.

Synthesizing a PPS can be accomplished either by chemically reacting an enzyme with a functionalized polymer or by chemically linking an enzyme to a functionalized polymer via a coupling agent.

Both natural and synthetic proteins can be used to form the PPS. Non-limiting examples of useful proteins include enzymes, hormones, toxins, antibodies, antigens, lectins, structural proteins, signal proteins, transport proteins, receptors, and blood factors. Proteins generally include at least one reactive site or substituent. For example, most naturally occurring proteins include at least one of the following functionalities: amine [(RNH$_2$), R(NH), C(NH), and (NH2)], sulfhydryl (RSH), carboxyl (RCOOH), and phenol (RC$_6$H$_4$OH). These reactive sites or substituents can be reacted with an appropriate functional group on a polymer or coupling agent.

Enzymes are proteins that can catalyze chemical reactions. Some preferred enzymes include those having biochemical activities such as chymotrypsin, cytochrome C, trypsin, subtilisin, horseradish peroxidase, soybean peroxidase, and glucose oxidase. Especially preferred enzymes are α-chymotrypsin, β-galactosidase, and chloroperoxidase. Enzymes may be isolated from plants, animals, and microorganisms including single-celled bacteria such as *Escherichia coli* (*E. coli*). Of the approximately several thousand different proteins within a single celled bacteria (e.g., there are greater than 3,000 in an *E. Coli* cell), specific enzymes therein can be isolated by splitting the cell and using conventional isolation techniques.

Some enzymes catalyze reactions because of the amino acid residues that form their polypeptide chains; an example is pancreatic ribonuclease. Other enzymes, however, require an additional chemical component called a cofactor for catalytic activity. The cofactor can be an inorganic compound or element, such as $Fe^{2+}$, $Mn^{2+}$, or $Zn^{2+}$ ions, or it may be a complex organic molecule called a coenzyme; coenzymes act as carriers of specific functional groups. Some enzymes require both a coenzyme and one or more metal ions for activity. In some enzymes, the coenzyme or metal ion is only loosely and transiently bound to the protein, but in others it is tightly and permanently bound via covalent chemical bonds, in which case it is called a prosthetic group. A complete catalytically active enzyme together with its coenzyme or metal ion is called a holoenzyme. Within the holoenzyme, the protein part of the enzyme is called the apoenzyme.

Functionalized polymers can derive from either natural or synthetic polymers. Useful synthetic polymers are plastics, solid powders, resins, and waxes that are linear and soluble in at least one nonpolar solvent such as chloroform, dimethylformide, or toluene. The polymers can be functionalized so that they react with a protein or coupling agent, or they may be synthesized to include such a functionality.

Without undue experimentation, those skilled in the art can select polymeric functional groups that will react with a corresponding reactive site on a protein or coupling agent. The desired functional groups can be incorporated into the polymer either by using specific initiators or terminators during polymer synthesis or by using conventional grafting techniques. Additionally, polymerizing certain monomers as part of a homopolymer or copolymer can yield the desired functionality.

Examples of useful polymeric functional groups include hydroxy groups (—OH), amine groups (RNH$_2$ and (R2NH), sulfhydryl groups (RSH), carboxyl groups (—COOH), and aldehyde groups [—C(O)H].

Some examples of linear polymers that can be modified to include a functional group include, but are not limited to, homopolymers and copolymers of α-olefins, α-β-ethylenically unsaturated carboxylic acids, vinyl aromatics, ethyl ethers, and combinations thereof. Exemplary α-olefins include ethylene, propylene, pentene 1-butene, 1-hexene, 4-methyl-1 pentene, 1-octene, 1-decene, or combinations thereof. Exemplary α-β-ethylenically unsaturated carboxylic acids include acrylic acid, methacrylic acid. Exemplary vinyl aromatics include styrene. Exemplary ethyl ethers include ethylene glycol, vinyl ethyl ether, vinyl acetate, and methyl methacrylate. Preferred polymers are polyethylene glycol, polystyrene, poly(methyl methacrylate), poly(vinyl acetate), and poly(vinyl ethyl ether).

Polymers having a variety of weights are useful in preparing a PPS. Polymers of varying molecular weights are generally selected based on the polymer's overall hydrophobicity as well as the enzyme's hydrophilicity. The polymer's hydrophobicity should promote the PPS's self-assembly at the polar-nonpolar biphasic liquid interface. Therefore, the weights of useful polymers may vary. Typical polymeric number-average molecular weights were determined by GPC and range from 100 Daltons (e.g., a monomer or oligomer) to 1,000,000 Daltons (e.g., high molecular-weight polymers).

As noted above, hydrophobicity is a factor in selecting an appropriate polymer length and weight. Hydrophobicity relates to a substance's compatibility with water. Quantitative measurements are based on the difference between the Hildbrand solubility measurements of water compared to that of the subject substance. Hildbrand solubility parameters are defined through the cohesive energy of materials and reflect their polarity (J. Brandrup and E. H. Immergut, Polymer Handbook, John Wiley & Sons, NY. 1989); they are commonly used to indicate the hydrophobicity of both liquids and polymers. Water has the highest solubility parameter and is assigned a numerical value of 47.9 $(MPa)^{1/2}$. Materials with lower numerical values are more hydrophobic. For example, methane has a value of 11 $(MPa)^{1/2}$, and is considered as very hydrophobic. Common hydrophobic solvents, for examples, may include: toluene (18.2), hexane (14.9), iso-octane (15.6), amyl ether (14.9), ethyl acetate (18.6), Chloroform (19.0); common hydrophilic solvents (and considered as water-miscible) may include: acetone (20.3), methanol (29.7), ethanol (26.0), acetonitrile (24.3), dimethyl sulfoxide (24.6). For polymers, similar solubility parameters are also available. For example, common hydrophobic polymers may include: polystyrene (17.52), poly(urethane) (20.5), poly(vinyl acetate) (19.13), poly(isobutene) (16.25), poly(butadiene) (17.19), natural rubber (16.2), and poly(ethylene) (15.76). Non-limiting examples of hydrophilic polymers may include: cellulose (32.02), poly(methacrylic acid) (27), poly(ethylene glycol) (25), and polyacrylonitrile (25.27). All the values cited here are in the same unit, $(MPa)^{12}$. Other factors, especially the formation of hydrogen bonds, may lead to some deviation from the nature of the materials as indicated by the use of the solubility parameters. However, in general, the solubility parameter is accurate to reflect the relative hydrophobicity of the polymers and solvents concerned in this invention.

Useful coupling agents include compounds that are otherwise inert except for preferably having at least two reactive functional groups, and at least one of the coupling agent's functional groups can react with an enzyme and at least another functional group can react with a functionalized polymer.

Examples of preferred enzymatic functional groups can be represented by the following formulas:

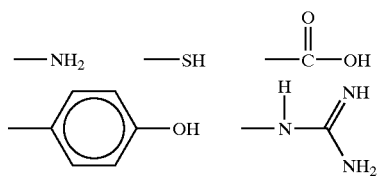

Examples of preferred coupling agents can be represented by the following formulas:

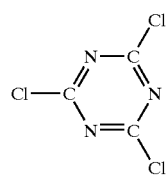

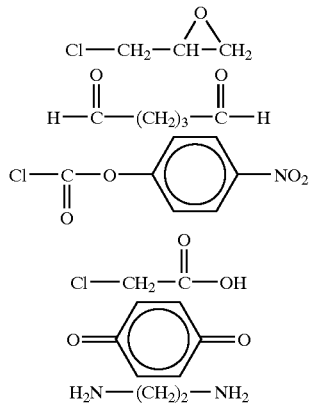

Examples of preferred polymeric functional groups can be represented by the following formulas:

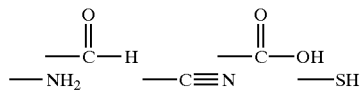

Non-limiting examples of liquids used in reactions involving and in preparing a PPS are polar solvents such as water and nonpolar solvents such as: toluene, ethyl acetate, hexane, isooctane, benzene, and mixtures thereof respectively.

A PPS can be synthesized by various methods. In one method, synthesis is carried out in a polar-nonpolar biphasic liquid medium where the functionalized polymers are dissolved in an organic solvent and the enzymes are dissolved in an aqueous solution. When an enzyme and functionalized polymer come into contact at a biphasic liquid interface, they can chemically bond and thereby form PPS. The resulting PPS, which is positioned at the liquid interface, is collected and purified by using separation techniques such as extraction, dialysis, ultra-filtration, precipitation, or size exclusion liquid chromatography.

In another method, the enzymes are ion paired with surfactants and then dissolved into a hydrophobic solution. Ion-pairing techniques are well known in the art, and an exemplary approach is disclosed in U.S. Pat. No. 5,914,367, which is herein incorporated by reference. The ion-paired proteins can then react with the functionalized polymers or inert coupling agents dissolved in the hydrophobic solvent. The resulting PPSs are isolated and purified in two steps. First, the PPSs are dissolved in a pure hydrophobic solvent and then water is contacted with the hydrophobic solution. Second, the solution in the vicinity of the interface is collected, and the PPSs therein are dried and washed. Alternatively, size-exclusion liquid chromatography can be used to isolate PPSs from the nonpolar solvent.

In yet another embodiment, a hydrophobic polymer solid is contacted with a polar solution comprising hydrophilic proteins. Preferably, the proteins are enzymes.

Several approaches can be employed in synthesizing a PPS by using a coupling agent. The coupling agent is first attached to the polymer and then the protein, or the coupling agent is first attached to the protein and then the polymer. Generally, the coupling agent and functionalized polymer are soluble in the organic phase, and it is therefore more efficient to first attach the coupling agent to the functionalized polymer. The hydrophilic protein can then be attached using emulsion or ion-pairing techniques.

A variety of reaction conditions can be employed in synthesizing the PPS. The selected conditions should preferably preserve the character of both the reactants and resulting PPS. Accordingly, those skilled in the art will be able to select appropriate reaction conditions without undue experimentation or calculation.

When synthesizing a PPS, enzymes, functionalized polymers, and/or coupling agents can typically withstand temperature ranges from about 0° C. to about 60° C.; temperatures are typically selected in light of the protein's thermostability. If enzyme modification is carried out in a nonpolar phase (e.g., by using ion-pairing techniques) or the protein is thermally stable at high temperatures, reactions can occur at temperatures up to about 100° C.

Reactions that couple the protein to the polymer, polymerization reactions, and interfacial chemical processing reactions can be conducted at ambient pressure (1 atmosphere) to save energy and equipment costs. However, should it become necessary, these reactions can be conducted at lower or higher pressures. For example, if a supercritical fluid, such as carbon dioxide, is used as a reaction solvent, then the pressure should be above 74 atmospheres.

As for reactions employing the PPS, the temperatures are generally within the tolerance of the enzymes, i.e., from about 0° C. to about 100° C. There is no limitation on pressure other than convenience and cost, although ambient pressure is favored in most cases. High pressures can be employed in order to accommodate super-critical fluids; some enzymes are stable at pressures up to 350 atmospheres (J. Kim and J. S. Dordick, *Biotechnology and Bioengineering, vol.* 42, p772, 1993).

Other reaction conditions such as pH, concentration, and stirring speed, can be adjusted as needed. The pH range depends on the enzyme's tolerance and the requirements of the desired reaction. Most enzymes perform best in a pH range from about 3 to about 8. Stirring is usually applied to accelerate the reaction, but should not be so fast as to degrade the protein's structure. Typically, about 200 to about 500 rotations-per-minute (rpm) is reasonable for most reactions concerned with this invention. Concentrations of proteins, substrates, polymers, solvents and other additives can be controlled at values satisfying the operational requirements.

The PPSs of this invention can catalyze a variety of reactions occurring in a polar-nonpolar biphasic liquid medium. When a PPS is employed, the reactants of chemical process are dissolved in either one or both of the liquids. Additionally, where the PPS's enzymatic substituent requires a cofactor(s) for catalytic activity, the cofactor(s) is dissolved in one or both of the liquids of the biphasic liquid medium.

As described above, the reactions catalyzed by the PPS take place within a biphasic polar-nonpolar liquid medium. Specifically, one of the phases is nonpolar and hydrophobic while the other is polar and hydrophilic. Where the two phases contact each other, an interface results, which is where the PPS positions itself. From the interface, the PPS can catalyze reactions between reactants in either one or both of the two phases. Biphasic polar-nonpolar liquid mediums include both layers and emulsified mediums.

A layered reaction medium exists where a polar and nonpolar solvent, e.g., liquid water and an organic liquid, are placed into contact with each other without any mixing or agitation. Because the phases are not agitated or mixed together, the two liquids will separate and form distinct layers having a single continuous interface.

An emulsified reaction medium occurs where an aqueous phase and organic phase are placed into contact with each other in the presence of mixing or agitation. The mixing or agitation yields spherical-like suspensions of at least one of the liquids the other liquid. In other words, the mixing or agitation, (e.g., shaking) causes droplets of one of the phases to be dispersed into the other phase. The total surface area between phases, i.e., interface area, within an emulsified system is advantageously greater than that of a layered system. Therefore, reaction rates are greater in the emulsified reaction medium due to the greater interface area, which is where the reactions occur. Other emulsion techniques, such as using ultrasonic devices, may be used to achieve an emulsified reaction medium.

In order to demonstrate the practice of the present invention, the following examples have been prepared and tested. The examples should not, however, be viewed as limiting the scope of the invention. The claims will serve to define the invention.

EXAMPLES

Example 1

Styrene monomer (5 ml) (EM; Gibstown, N.J.) was dissolved in toluene (1 ml). 2,2'-azobis[2-methyl-N(2-hydroxyethyl)propionamide]) (0.1 grams)(VA-086; Waco Pure Chemical Industries, Ltd.; Osaka, Japan) dissolved in N,N-dimethylformamide (4 ml) (DMF; Sigma; St. Louis, Mo.) was added to the mixture. The reaction system was then incubated in a water bath set at 72° C. for 24 hours. After the reaction, the polystyrene was precipitated and washed with methanol. The number average molecular weight of the polystyrene, as determined by Gel Permeation Chromatography analysis using polystyrene standards, was about 143,000.

The PST prepared above (0.5 g) was dissolved in toluene (8 ml). After cooling to 4° C., 4-dimethylaminopyridine (0.01M)(Sigma; Steinheim, Germany) was added. Then NPC (0.01M) (Aldrich; Milwaukee, Wis.), which was dissolved in anhydrous methylene chloride, was added slowly under magnetic stirring. After 5 hours, the reaction mixture, which contained a white precipitate that was believed to be 4-dimethylaminopyridine hydrochloride, was centrifuged. The supernatant was precipitated and washed with methanol.

As prepared above, the PST attached to the coupling agent (0.1 g) was dissolved in toluene (3 ml). A sodium borate buffer (3 ml of 0.2M @ pH 8.2), which contained α-chymotrypsin and β-galactosidase (9 mg) (Sigma; St. Louis, Mo.), was added to the solution. The reaction system was shaken at room temperature for about 24 hours. During this coupling process, the enzymatic activity of the native enzyme was measured, and no decrease of activity was detected.

The enzyme loading of the conjugates was obtained by mass balance of the system's native enzyme both before and after modification. Specifically, the enzyme loading of the polystyrene-α-chymotrypsin surfactant was 0.0393 mg enzyme/gram of polystyrene, and 0.842 mg enzyme/gram of polystyrene for the polystyrene-β-galactosidase surfactant. In conducting the foregoing analysis, two types of proteins assay methods were employed. The first was the Bio-Rad™ protein assay wherein a Bio-Rad™ protein assay direagent concentrate was diluted ten-fold in distilled water. 2.5 ml of reagent was added to a 5 ml UV cuvette, and then a 0.05 ml sample was introduced. Absorbance of the solution at 595 nm was measured on a UV-Vis spectrometer (UV-1601 Shimadzu), by using lyophilized globulin (Bio-Rad™ protein assay standard I) as the standard. The second assay was conducted in accordance with the method outlined by Makoto Matsushita et al. (*Determination of proteins by a reverse biuret method combined with the copper-bathocuproine chelate reaction*. Clinica Chimica Acta, 1993[216]: p.103–11), based on UV-Vis spectrometer (UV-1601 Shimadzu) at 485 nm, by using lyophilized globulin (Bio-Rad™ protein assay standard I) as the standard.

Hydrolysis of SAAPP (n-succinyl-ala-ala-prophe p-nitroanilide) by both native and modified α-chymotrypsin is performed in 2.5 ml pH 8.2 sodium borate buffer solution containing 0.51 mM SAAPP. 10 μl to 100 μl buffer solution of native α-chymotrypsin (1 mg/ml) is added. The reaction rate is measured by UV spectrometer (UV-1601 Shimadzu) at 410 nm. As for modified α-chymotrypsin, the reaction is carried out in toluene-buffer bi-phasic system. 0.0509 g modified α-chymotrypsin is dissolved into 2.5 ml toluene while the volume of buffer and substrate concentration are the same as those for native α-chymotrypsin.

Transesterification reaction of APEE (n-acetyl-phenylalanine ethyl ester) with n-propanol by native and modified α-chymotrypsin are carried out in the mixture of toluene and hexane (volume ratio equals 1:1). The concentrations of APEE and n-propanol are 0.01 M and 0.5 M respectively. 1 mg native α-chymotrypsin is dispersed in the reaction medium, while 0.317 g modified α-chymotrypsin is dissolved in the solvent. The reaction is monitored by gas chromatography (Shimadzu, GC-17A) using an FID detector.

Both lactose hydrolysis in aqueous buffer solution and transgalactosylation of lactose with hexanol in toluene-buffer bi-phasic system are carried out to evaluate the activity of modified β-galactosidase. 0.3 mg native β-galactosidase and 0.013 g modified β-galactosidase are added to 2 ml pH 4.5 buffer solutions containing 480 mg lactose respectively. Then, 4 ml hexyl alcohol dissolved in 7 ml toluene is added. The reaction systems are shaken at room temperature. At certain time interval, 1 ml sample is taken out from organic phase and dried. The product is dissolved in HPLC mobile phase (20% water and 80% acetonitrile, v:v) and analyzed by HPLC (high pressure liquid chromatography) (Shimadzu, SCL-10A vp) using RID (Shimadzu, RID-10A) detector and Waters Carbohydrate Analysis column. Interfacial transgalactosylation reaction modified by β-galactosidase is carried out in a reactor with inner radius of 6.632 cm. The volume ratio of aqueous phase and organic phase is 3.6:1. Modified β-galactosidase is partitioned at the interface of the bi-phasic system with 40% (v) hexanol in toluene phase and lactose (concentration range from 0.05 M up 0.7 M) in aqueous phase.

The polymer-protein surfactant comprises both a hydrophilic head and hydrophobic tail. When immersed in a bi-phasic system wherein one of the phases is an aqueous phase and the other is an organic or hydrophobic phase, the polymer-protein surfactant's hydrophobic polymer tail stretches to the organic solvent while the hydrophilic head embeds in the aqueous solution. Bio-Rad protein assay is used to indicate the location of the enzyme within the bi-phasic environment; the dye turns blue as it contacts with enzyme either in free or modified form. Upon performing this test, the α-chymotrypsin enzyme with the hydrophobic polystyrene tail displayed a high affinity for partitioning at the interface of the organic-aqueous bi-phasic system. Similar results were obtained for the β-galactosidase with the polystyrene tail.

Hydrolysis of n-succinyl-ala-ala-prophe p-nitroanilide in aqueous buffer solution (borate, pH 8.2) and transesterification of n-acetyl-$_L$-phenylalanine ethyl ester with n-propanol in toluene-hexane mixture are carried out by both the native and modified α-chymotrypsin to evaluate the activity of the modified enzyme. The modified α-chymotrypsin catalyst enzyme retained most of its activity in aqueous solution in catalyzing the hydrolysis of n-succinyl-ala-ala-prophe p-nitroanilide. The transesterification reaction in organic solvent catalyzed by the modified α-chymotrypsin is about 2,000-fold faster than if the reaction is catalyzed by the native enzyme. The fact that the reaction rate is 2,000-fold faster than that of the native enzyme may be attributed to the modified enzyme's improved structural stability as well as its proximity to the reactants in the organic phase.

The half residual activity time of modified α-chymotrypsin extends 3 folds over that of its native counterpart; as for modified β-galactosidase the time extends 1.8 folds over its native counterpart. The enzyme's overall stability enhancement is likely provided by the polymer tail.

The initial reaction rate is 150-fold higher when catalyzed by the modified β-galactosidase as opposed to its native counterpart. Bear in mind that a biphasic system was employed in carrying out the reaction. The polymer-protein surfactant, namely polymer-β-galactosidase, assembles at the interface of the reaction media. Substrates are reactants that diffuse from both the aqueous and hydrophobic phases to the interface where the catalyzed reaction occurs. And the product then diffuses from the interface back into the bulk organic solvent. The experimental results showed considerably improved reaction rates by using the modified β-galactosidase polymer protein surfactant as opposed to its native counterpart.

Styrene monomer (5 ml) (EM; Gibstown, N.J.) was dissolved in toluene (1 ml). 2,2'-azobis[2-methyl-N(2-hydroxyethyl)propionamide]) (0.1 grams)(VA-086; Waco Pure Chemical Industries, Ltd.; Osaka, Japan) dissolved in N,N-dimethylformamide (4 ml) (DMF; Sigma; St. Louis, Mo.) was added to the mixture. The reaction system was then incubated in a water bath set at 72° C. for 24 hours. After the reaction, the polystyrene was precipitated and washed with methanol. The number average molecular weight of the polystyrene, as determined by Gel Permeation Chromatography analysis using polystyrene standards, was about 78,000.

The PST prepared above (2 g) was dissolved in 10 ml epichlorohydrin, and stored at room temperature for 24 hours. The reaction was terminated by evaporating the residual epichlorohydrin, and the activated polystyrene product is then washed using methanol.

0.05 g of polystyrene coupled to epichlorohydrin was added into 5 ml 0.2M citrate buffer (pH 4.5). Then 75 μl chloroperoxidase is added to start the reaction. The reaction mixture is shaken at speeds of 200 rpm at room temperature for 20 hours.

The polymer-protein surfactant is separated by filtration and washed with citrate buffer (pH4.5) until no free enzyme is detected in the solution. The polymer-protein surfactant is stored at 4° C.

Various modifications and alterations that do not depart from the scope and spirit of this invention will become apparent to those skilled in the art. This invention is not to be duly limited to the illustrative embodiments set forth herein.

What is claimed is:

1. A polymer-protein surfactant formed by a process comprising the steps of:
   providing a biphasic liquid medium that comprises one polar phase and one non-polar phase in contact with each other;
   adding a protein to said polar phase;
   adding a functionalized polymer to said non-polar phase;
   providing a hydrophilic end to said protein at an interface between said polar phase and said non-polar phase; and
   reacting the functionalized polymer with the hydrophilic end of said protein at the interface to form the protein-polymer surfactant.

2. A polymer-protein surfactant comprising a hydrophilic protein substituent and a hydrophobic polymeric substituent arranged to provide said polymer-protein surfactant with a hydrophobic end portion and a hydrophilic end portion; wherein the protein is an enzyme.

* * * * *